United States Patent
Pitsch et al.

(10) Patent No.: US 12,128,362 B2
(45) Date of Patent: Oct. 29, 2024

(54) METHOD AND INSTALLATION FOR TESTING THE INTEGRITY OF A CAPILLARY DIALYZER

(71) Applicant: FRESENIUS MEDICAL CARE DEUTSCHLAND GMBH, Bad Homburg (DE)

(72) Inventors: Stefan Pitsch, Quierschied (DE); Manuel Wilhelm, St. Ingbert (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 261 days.

(21) Appl. No.: 17/773,070

(22) PCT Filed: Nov. 3, 2020

(86) PCT No.: PCT/EP2020/080843
§ 371 (c)(1),
(2) Date: Apr. 29, 2022

(87) PCT Pub. No.: WO2021/089565
PCT Pub. Date: May 14, 2021

(65) Prior Publication Data
US 2022/0410074 A1    Dec. 29, 2022

(30) Foreign Application Priority Data

Nov. 4, 2019    (DE) .................... 10 2019 129 664.1

(51) Int. Cl.
*B01D 65/10*    (2006.01)
*A61M 1/16*    (2006.01)
(Continued)

(52) U.S. Cl.
CPC ......... *B01D 65/102* (2013.01); *A61M 1/1627* (2014.02); *A61M 1/3626* (2013.01);
(Continued)

(58) Field of Classification Search
None
See application file for complete search history.

(56) References Cited

U.S. PATENT DOCUMENTS

| | | | |
|---|---|---|---|
| 5,910,250 A * | 6/1999 | Mahendran | B01D 63/0222 210/321.89 |
| 6,324,898 B1 | 12/2001 | Cote et al. | |
| 7,378,024 B2 * | 5/2008 | Bartels | B01D 65/02 210/636 |

FOREIGN PATENT DOCUMENTS

| | | |
|---|---|---|
| DE | 4215585 A1 | 11/1993 |
| JP | 3-81547 U | 8/1991 |

(Continued)

OTHER PUBLICATIONS

International Search Report and Written Opinion issued in corresponding International Patent Application No. PCT/EP2020/080843 (with English translation of International Search Report) dated Feb. 9, 2021 (15 pages).

(Continued)

*Primary Examiner* — Peter J Macchiarolo
*Assistant Examiner* — Jermaine L Jenkins
(74) *Attorney, Agent, or Firm* — Kilyk & Bowersox, P.L.L.C.

(57) ABSTRACT

A method is presented for checking the integrity of a hollow-fibre fluid filter, in particular a hollow-fibre dialyzer (1), which is constructed from a plurality of hollow fibres (15) enclosed by a membrane, with the steps of: perfusing the inside or outside of the hollow fibres (15) with a fluid, supplying the outside or inside of the hollow fibres (15) with a gas, wherein the gas has a higher pressure than the fluid, and determining a quantity of the gas which penetrates into the fluid through holes in the membrane. The method is characterized in that, after flowing through the hollow-fibre fluid filter (1), the fluid is channelled through a bubble trap (Continued)

(30), and in that a volume of gas (41) collecting in the bubble trap (30) during a predefined or predefinable reference period is determined. Furthermore, equipment for checking the integrity of a hollow-fibre fluid filter (1) is presented.

21 Claims, 3 Drawing Sheets

(51) Int. Cl.
    *A61M 1/36*     (2006.01)
    *B01D 61/24*     (2006.01)
    *B01D 63/02*     (2006.01)

(52) U.S. Cl.
    CPC ............ *B01D 61/244* (2022.08); *B01D 63/02* (2013.01); *A61M 2205/3306* (2013.01); *A61M 2205/3331* (2013.01); *A61M 2205/705* (2013.01); *A61M 2209/02* (2013.01)

(56) References Cited

FOREIGN PATENT DOCUMENTS

| | | |
|---|---|---|
| JP | 6-178925 A | 6/1994 |
| JP | 10-225628 A | 8/1998 |
| JP | 200199775 A | 4/2001 |
| WO | WO-2007080260 A1 * | 7/2007 ............. B01D 63/02 |

OTHER PUBLICATIONS

Office Action dated Aug. 29, 2024 for counterpart Japanese Application No. 2022-524201 (in English-5 pages).

* cited by examiner

METHOD AND INSTALLATION FOR TESTING THE INTEGRITY OF A CAPILLARY DIALYZER

This application is a National Stage Application of PCT/EP2020/080843, filed Nov. 3, 2020, which claims priority to German Patent Application No. 10 2019 129 664.1, filed Nov. 4, 2019.

The invention relates to a method for checking the integrity of a hollow-fibre fluid filter, in particular a hollow-fibre dialyzer, which is constructed from a plurality of hollow fibres enclosed by a membrane, with the steps of: perfusing the inside or outside of the hollow fibres with a fluid, supplying the respectively corresponding outside or inside of the hollow fibres with a gas, wherein the gas has a higher pressure than the fluid, and determining a quantity of the gas which penetrates into the fluid through holes in the membrane.

Furthermore, the invention relates to equipment for checking the integrity of a hollow-fibre fluid filter, in particular a hollow-fibre dialyzer, which is constructed from a plurality of hollow fibres enclosed by a membrane, comprising: a flushing system which is set up to channel a fluid through the interior or exterior of the hollow fibres of a hollow-fibre dialyzer to be checked, a gas pressure system which is set up to supply the respectively corresponding exterior or interior of the hollow fibres of the hollow-fibre fluid filter to be checked, in particular of the hollow-fibre dialyzer, with a gas, wherein the pressure of the gas is higher than the pressure of the fluid, and a measuring device for the determination of a quantity of gas penetrating into the fluid through holes in the membrane during a predefined or predefinable reference period.

Hollow-fibre dialyzers are used in medicine to filter harmful substances from the blood of patients with reduced kidney function. For this purpose, the blood contaminated with harmful substances is brought into contact with a dialysis fluid via a semi-permeable membrane. The dialysis fluid has an extremely low concentration of the harmful substances to be removed, such as e.g. urea, with the result that the harmful substances diffuse through the membrane into the dialysis fluid due to a concentration gradient or pass into the dialysis fluid due to convective effects. At the same time, the membrane is at least partially impermeable for other blood components such as blood plasma or particulate components. This procedure is called dialysis.

Other hollow-fibre fluid filters are often likewise used in medical technology, for example in order to prepare untreated water for dialysis. Such filters can also be used elsewhere in water treatment.

In particular, for effective blood purification a large membrane surface is required. For this, known hollow-fibre dialyzers have a plurality of hollow fibres, for example approx. 10,000. The walls of the hollow fibres are formed by a semi-permeable membrane. The hollow fibres are placed in a tube-like volume as a loose bundle.

During the dialysis, the patient's blood is channelled through the hollow fibres, while the dialysis fluid flows through the tube-like volume. The blood and dialysis fluid preferably flow in opposite directions, i.e. the dialyzer works according to the counterflow principle.

As a rule, hollow-fibre dialyzers are provided as sterile disposable products and to this end are subjected to a sterilization process after production. A steam sterilization is often used here. Other hollow-fibre fluid filters are frequently also sterilized using steam.

Since the hollow fibres have a very small wall thickness, it can be the case that holes appear in individual hollow fibres during the production of a hollow-fibre fluid filter or hollow-fibre dialyzer. In addition, holes can form as a result of various other types of damage. As a result of such holes, during the dialysis blood can pass out of the hollow fibres into the dialysis fluid on the one hand and dialysis fluid can penetrate into the blood on the other hand. Neither is desirable, wherein in particular the penetration of dialysis fluid into the patient's blood in large quantities can be problematic physiologically.

In order to identify hollow-fibre fluid filters, in particular hollow-fibre dialyzers, with corresponding holes they are subjected to a check. Since holes can also form during the sterilization the check is carried out immediately after the sterilization, as a rule.

In a known checking method for hollow-fibre dialyzers, a test fluid, in most cases water, is channelled through the hollow fibres, while at the same time a gas is introduced into the volume surrounding the hollow fibres. Here, the gas is at a higher pressure than the fluid, with the result that it can penetrate into the hollow fibres through any holes.

The gas forms small bubbles in the fluid, which are flushed out of the hollow fibres by the fluid stream. In order to detect the bubbles, the fluid stream is then channelled through a sight glass, which is observed by a camera.

However, a quantitative determination of the quantity of gas that has penetrated is difficult with this method since each individual bubble has to be evaluated as it flows past, and the form of the bubbles cannot be fully recorded. In addition, the sight glass must be monitored over a relatively long period in order to achieve sufficient sensitivity. If, in addition, the check is effected on a pulsed conveyor over several stopping positions, the observation must be interrupted and individual bubbles can be easily overlooked.

An object of the invention is therefore to provide an improved method and improved equipment for checking the integrity of a hollow-fibre fluid filter, in particular a hollow-fibre dialyzer.

This object is achieved according to a first aspect of the invention by a method for checking the integrity of a hollow-fibre fluid filter, in particular a hollow-fibre dialyzer, which is constructed from a plurality of hollow fibres enclosed by a membrane, with the steps of: perfusing the inside of the hollow fibres with a fluid and supplying the outside of the hollow fibres with a gas, or perfusing the outside of the hollow fibres with a fluid and supplying the inside of the hollow fibres with a gas, wherein in each case the gas has a higher pressure than the fluid, and determining a quantity of the gas which penetrates into the fluid through holes in the membrane, which method is developed in that, after flowing through the hollow fibres, the fluid is channelled through a bubble trap, and in that a gas volume collecting in the bubble trap during a predefined or predefinable reference period is determined.

The individual gas bubbles entering into the hollow fibres or exiting from the hollow fibres are here collected in the bubble trap, with the result that they form a largely, preferably uniform gas volume. This gas volume can be determined easily, with the result that an exact quantitative determination of the penetrating quantity of gas is possible even without a long-term observation.

It is thus possible to supply the outside or the inside of the hollow fibres with the gas, wherein the respectively complementary side is then supplied with the fluid.

The hollow-fibre fluid filter is preferably a hollow-fibre dialyzer. The membranes of these dialyzers have a particularly small wall thickness of from 10 to 50 µm, preferably 15 to 35 µm, with the result that there is a particular susceptibility to leaks. Moreover, the requirements for dialyzers to be leak-free are particularly high due to the required patient safety. At the same time, it has been shown that the exiting gas bubbles are particularly fine and thus visually very difficult to detect as individual bubbles. The method according to the invention can thus be used particularly advantageously for hollow-fibre dialyzers.

In particular in the case of hollow-fibre dialyzers containing membranes with the selective surface in the lumen of the membrane it is preferred to supply the outside with gas and the inside with fluid. It is thereby possible to guarantee a particularly gentle treatment of the lumen of the membrane during the leak test.

In an advantageous development of a method according to the invention, an initial value of the gas volume can be determined at the start of the reference period, a final value of the gas volume can be determined at the end of the reference period and the quantity of gas that has penetrated into the hollow fibres in the reference period can be determined from the difference between the initial value and the final value.

Water can preferably be used as fluid. The use of water as test fluid can prevent any solvent mixtures accumulating from the method as waste. In addition, residual quantities of water can remain in a filter, in particular in a dialyzer, after the test has been carried out without damaging the health of the patient.

In a particularly advantageous permutation of a method according to the invention, a line system comprising the bubble trap and the hollow-fibre fluid filter, in particular the hollow-fibre dialyzer, can be supplied with steam before the start of the check.

Supplying the line system with steam can be effected in order to sterilize the hollow-fibre fluid filter, in particular the hollow-fibre dialyzer, as well as line sections temporarily connected to it. The steam fills the bubble trap, wherein any gas contained therein from a preceding checking procedure is replaced. As soon as the steam cools down and condenses, the steam volume in the bubble trap collapses, with the result that the latter can be almost completely filled with water, without a valve being needed for this purpose.

The determination of the volume of gas collected in the bubble trap can be effected visually in a preferred permutation of a method according to the invention. For this, the bubble trap can have a transparent section and, for the determination of the volume of gas collected in the bubble trap, the location of a fluid surface in the transparent section can be assessed. Visual methods have proven to be particularly robust, i.e. not very error-prone, and simple.

After visual detection, the location of the fluid surface in the transparent section can be determined in an uncomplicated manner by means of image processing.

In an advantageous embodiment of a method according to the invention, at least one first camera image of the transparent section can be captured at the start of the reference period and the initial location of the fluid surface can be determined by means of an image evaluation method, at least one second camera image of the transparent section can be captured at the end of the reference period and the final location of the fluid surface can be determined by means of an image evaluation method, and the volume of gas collected can be determined from the initial location of the fluid surface and the final location of the fluid surface.

The first and the second camera image can preferably be captured using a transmitted light method. Transmitted light methods can be implemented with low equipment costs accompanied by a low space requirement in a compact manufacturing system.

According to a preferred embodiment, the illumination can be effected by means of a fluorescent film, which is illuminated with excitation light of a first wavelength, and which, in response to the illumination with excitation light, emits fluorescent light of a second wavelength, wherein the second wavelength is greater than the first wavelength, and the camera images can be captured through a filter that is not transparent for light of the first wavelength.

In the case of a corresponding illumination, for one thing, disruptive reflections on the surfaces of the transparent section are reduced to a minimum, while at the same time camera and light source can be arranged on the same side of the transparent section. The space requirement for the measuring device is further reduced hereby.

A flow system comprising the bubble trap and the hollow-fibre dialyzer can be arranged on a conveyor operated in a pulsed manner, which is moved on at least one conveying position during the reference period.

The object is achieved according to a further aspect of the invention by equipment for checking the integrity of a hollow-fibre fluid filter, in particular a hollow-fibre dialyzer, which is constructed from a plurality of hollow fibres enclosed by a membrane, comprising a flushing system which is set up to channel a fluid through the interior of the hollow fibres of a hollow-fibre fluid filter to be checked, and a gas pressure system which is set up to supply the exterior of the hollow fibres of the hollow-fibre fluid filter to be checked with a gas, or a flushing system which is set up to channel a fluid through the exterior of the hollow fibres of a filter to be checked, and a gas pressure system which is set up to supply the interior of the hollow fibres of the filter to be checked with a gas, wherein in each case the pressure of the gas is higher than the pressure of the fluid, and a measuring device for the determination of a quantity of gas penetrating into the fluid through holes in the membrane during a predefined or predefinable reference period, which equipment is developed in that the flushing system comprises a bubble trap arranged downstream of the hollow-fibre fluid filter, and in that the measuring system is set up to determine a volume of gas collecting in the bubble trap during a predefined or predefinable reference period.

It is thus possible to supply the outside or the inside of the hollow fibres with the gas, wherein the respectively complementary side is then supplied with the fluid.

The hollow-fibre fluid filter is preferably a hollow-fibre dialyzer. The membranes of these dialyzers have a particularly small wall thickness of from 10 to 50 µm, preferably 15 to 35 µm, with the result that there is a particular susceptibility to leaks. Moreover, the requirements for dialyzers to be leak-free are particularly high.

In particular in the case of hollow-fibre dialyzers containing membranes with the selective surface in the lumen of the membrane it is preferred to supply the outside with gas and the inside with fluid. It is thereby possible to guarantee a particularly gentle treatment of the lumen of the membrane during the leak test.

In an advantageous embodiment of equipment according to the invention, the measuring device can be set up to determine an initial value of the gas volume at the start of the reference period, to determine a final value of the gas volume at the end of the reference period, and to determine the quantity of gas that has penetrated into the hollow fibres in the reference period from the difference between the initial value and the final value.

In a particular embodiment, the bubble trap has a trapping section in the flow channel of the test fluid, with the result that the flow rate of the test fluid decreases at least briefly, for example for 100 ms to 10 s. Bubbles can thereby be released from the test fluid particularly effectively and be fed to the volume detection system. The bubbles are preferably channelled through an upper wall of the trapping section to a sight glass. The upper wall is preferably formed tapered.

According to a further design of equipment according to the invention, the measuring device can be set up to determine the volume of gas collecting in the bubble trap visually. For this, the bubble trap can have a transparent section and the measuring device can be set up, for the determination of the volume of gas collected in the bubble trap, to assess the location of a fluid surface in the transparent section.

In a preferred embodiment of equipment according to the invention, the measuring device can comprise at least one camera and one image evaluation system. The measuring device can comprise at least one fluorescent film and at least one source for excitation light.

As an alternative to the visual detection system, an alternative fill-level detection system can also be provided, for example using an ultrasonic fill-level sensor.

In a further embodiment of the invention, the equipment can be a component of a conveying system driven in a pulsed manner, which comprises several conveying elements, wherein each conveying element is provided for receiving at least one hollow-fibre fluid filter, in particular a hollow-fibre dialyzer, and wherein each conveying element comprises, for each hollow-fibre fluid filter to be received, a bubble trap which is movable along the conveying system together with the hollow-fibre fluid filter.

The measuring device can comprise a first camera which is arranged stationary adjacent to a conveying path of the conveying system. The measuring device can furthermore comprise a second camera which is arranged stationary adjacent to the conveying path of the conveying system. The first and/or the second camera can preferably be arranged adjacent to a stopping position of the conveying system.

The conveying system can be a circular conveyor.

The invention is explained in more detail below with reference to some exemplary figures, wherein the embodiments represented in the figures are only intended to serve for a better understanding of the invention, without limiting it.

There are shown in.

Figure 1:
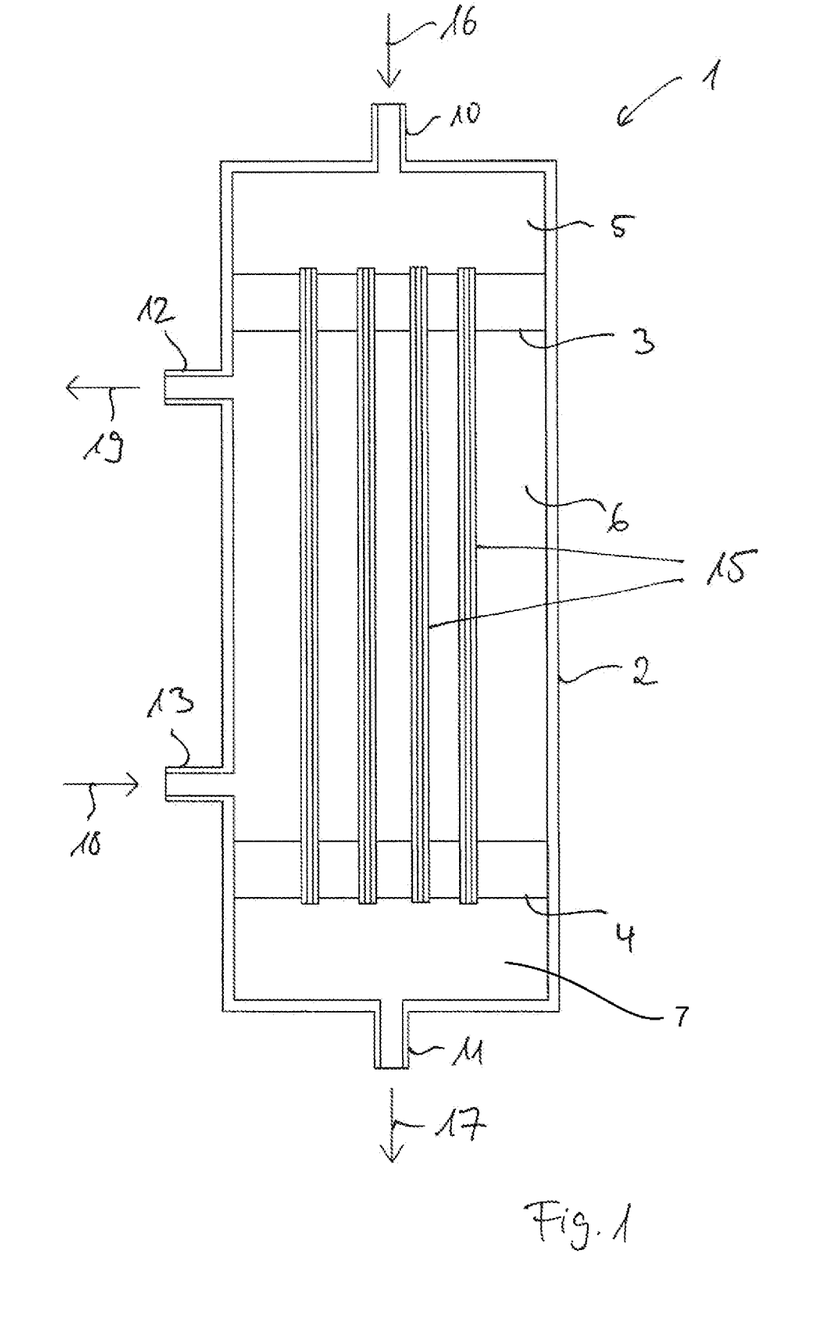
FIG. 1: a hollow-fibre dialyzer as an example of a hollow-fibre fluid filter in a simplified sectional representation.

A hollow-fibre dialyzer 1 is depicted in a simplified sectional representation in FIG. 1. The hollow-fibre dialyzer 1 consists of an approximately cylindrical housing 2, which is divided into three chambers 5, 6, 7 by sealing inserts 3, 4. Deviating from the embodiment example, a hollow-fibre fluid filter can also be provided instead of a hollow-fibre dialyzer.

The end chambers 5, 7 each have one connecting piece 10, 11. The middle chamber 6 has two connecting pieces 12, 13, which are each arranged close to the sealing inserts 3, 4. The connecting pieces 10, 11, 12, 13 can be "Luer lock" connections, for example.

Hollow fibres 15 run from the chamber 5, through the sealing inserts 3, 4 and the middle chamber 6, into the chamber 7. The representation of the hollow fibres 15 in FIG. 1 is greatly simplified. Instead of the four hollow fibres represented in FIG. 1, a hollow-fibre dialyzer usually has up to 18,000 hollow fibres, which are not completely straightened out as a rule. The wall thickness of the hollow fibres 15 can be approx. 10-50 µm, in particular 15 to 35 µm, the internal diameter of the hollow fibres 15 can be approx. 180 to 300 µm. The walls of the hollow fibres 15 consist of a biocompatible semi-permeable membrane. The membrane preferably comprises a polysulfone material, which is modified with polyvinylpyrrolidone (PVP).

If the filter is used for the processing of untreated water, this the membrane is also preferably hydrophilic, with the result that there is good wettability, in particular with water.

During the dialysis, blood is pumped through the connecting piece 10 into the chamber 5 along the arrows 16, 17 and then flows through the interior of the hollow fibres 15 into the chamber 7. From there, the blood is released again through the connecting piece 11 and fed back to the patient.

In parallel, dialysis fluid is channelled, along the arrows 18, 19, through the connecting piece 13 into the middle chamber 6, where it flows alongside the hollow fibres 15 against the direction of flow of the blood, before it is released again through connecting piece 12. In the process, toxins, such as for example urea, diffuse out of the blood through the membrane envelope of the hollow fibres 15 into the dialysis fluid. The blood is thereby purified.

For the effective and safe functioning of the hollow-fibre dialyzer 1 it is necessary for the flow paths for blood and dialysis fluid to be adequately sealed with respect to each other. Holes can allow an uncontrolled transfer of dialysis fluid into the blood and, conversely, a loss of blood into the dialysis fluid, which is physiologically undesirable.

Some possible sources of holes are mechanical faults in the membrane envelopes which can form during the extrusion of the hollow fibres 15, inadequate sealing between the sealing inserts 3, 4 and the hollow fibres 15 or the housing 2, or broken hollow fibres 15. Corresponding faults can arise during the manufacture of the hollow-fibre membranes, the manufacture of the hollow-fibre dialyzer 1 or during a subsequent sterilization.

The hollow-fibre dialyzer 1 needs to be sterilized because it comes into contact with the patient's blood during the dialysis. A popular method of sterilization is steam sterilization, in which hot steam is channelled through the hollow-fibre dialyzer 1. In that process, the steam flows through both the flow path of the blood and the flow path of the dialysis fluid, with the result that all surfaces in the hollow-fibre dialyzer are heated, for example to above 124° C., and any pathogens present are killed.

Figure 2:
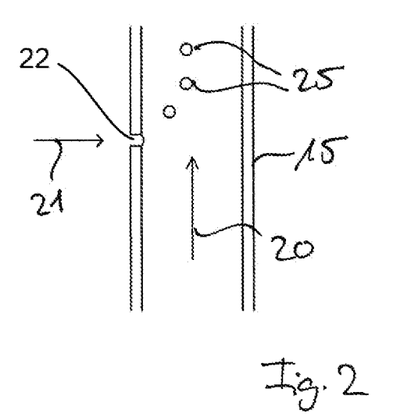
FIG. 2: a hollow fibre with a hole.

In order to exclude hollow-fibre dialyzers with holes from use, the hollow-fibre dialyzers are subjected to a tightness test after sterilization. The test principle is represented in FIG. 2.

For this, a test fluid, usually water, is channelled through the hollow fibres 15 in the direction of the arrow 20, while at the same time a test gas, e.g. air, is introduced into the chamber 6. Deviating from the embodiment example, it can also be provided that the test fluid is introduced into the chamber 6, while the test gas is channelled into the hollow fibres 15. In the process, the test gas in each case is at a higher pressure than the test fluid, which is indicated by the arrow 21. If the hollow-fibre dialyzer 1 now has a hole 22, the test gas can penetrate into the test fluid through this hole 22, and form bubbles 25 there. These bubbles are flushed out of the hollow fibre 15 with the test fluid and can then be detected.

Figure 3:
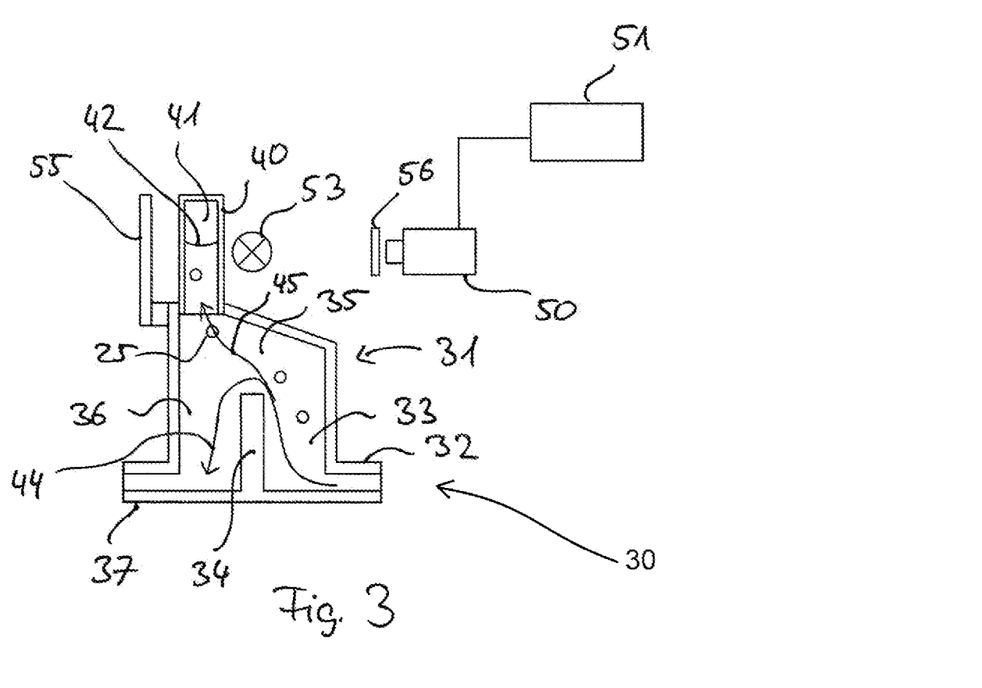
FIG. 3: a measuring device with a bubble trap.

For the qualitative and quantitative detection of the bubbles 25, the test fluid is channelled through a bubble trap 30 after passing through the hollow-fibre dialyzer 1. This is represented in FIG. 3.

The bubble trap 30 consists of a flow chamber 31, into which the test fluid flows through an inlet 32. Adjoining the inlet 32, the flow chamber has a rising section 33 which is delimited by a separator 34. Above the separator 34, the ascending section 33 merges into a trapping section 35. Following the trapping section 35 is a falling section 36 which merges into an outlet 37.

The trapping section 35 is designed such that the flow rate of the test fluid decreases briefly here. The bubbles 25 are released from the flow of the test fluid and are channelled by a tapered upper wall of the trapping section 35 to a sight glass 40.

In the sight glass 40, the bubbles 25 collect to form a cohesive gas volume 41. A boundary surface 42, which is used for the visual measurement of the gas volume 41, forms between the gas volume 41 and the test fluid.

The flow paths of the test fluid and of the bubbles 25 are indicated in the figure by arrows 44, 45.

For the measurement of the gas volume 41, the sight glass 40 is observed by a camera 50, and the location of the boundary surface 42 is determined by an image processing unit 51 on the basis of one or more consecutively captured images of the camera.

In order to suppress reflections, the visual measurement of the gas volume 41 is carried out using a transmitted light method. Since, however, for construction reasons, little space is available on the reverse side of the sight glass 40, represented on the left in FIG. 3, the camera 50 and a light source 53 must nevertheless be arranged on the same side of the sight glass 40. The light source 53 is arranged such that it does not obscure the view of the camera 50 onto the sight glass 40. For this, the light source 40 can be arranged slightly offset vertically or horizontally, or the light source 40 can be realized as a ring light arranged around the line of sight of camera 40.

In order to be able to work with transmitted light regardless, a fluorescent film 55 is arranged behind the sight glass 40. The light source 53 emits excitation light of a first wavelength, for example in the blue spectral range, some of which is reflected by the sight glass 40 in the direction of the camera 50. However, the majority of the excitation light is incident on the fluorescent film 55 and is there converted into fluorescent light of a second wavelength, for example in the orange spectral range. The fluorescent light is radiated in the direction of the sight glass 40 and of the camera 50.

Arranged in front of the objective lens of the camera 50 is a colour filter 56, which is not transparent for the short-wavelength excitation light and is transparent for the fluorescent light. As a result, the excitation light reflected on the sight glass 40 does not reach the camera 50, and the image captured is free of disruptive reflections. On a correspondingly captured image it is possible at little cost by means of well-known methods of image evaluation to detect the boundary surface 42 and determine its location. From the location of the boundary surface 42, the gas volume 41 can in turn be determined easily.

A corresponding fluorescent film can be obtained, for example, from Keyence Corporation under the product name "CA-DWC30".

The sterilization and checking of hollow-fibre dialyzers is effected on a conveyor working in a pulsed manner, for example a circular conveyor. Such a circular conveyor 60 is represented schematically in FIG. 4. The circular conveyor 60 comprises a plurality of individual receivers 61, 62 in each case for one or more hollow-fibre dialyzers 1. For each hollow-fibre dialyzer 1 to be received, each of the receivers 61, 62 comprises a bubble trap 30, the sight glasses 40 and the fluorescent films 55 of which are visible here in each case.

Figure 4:
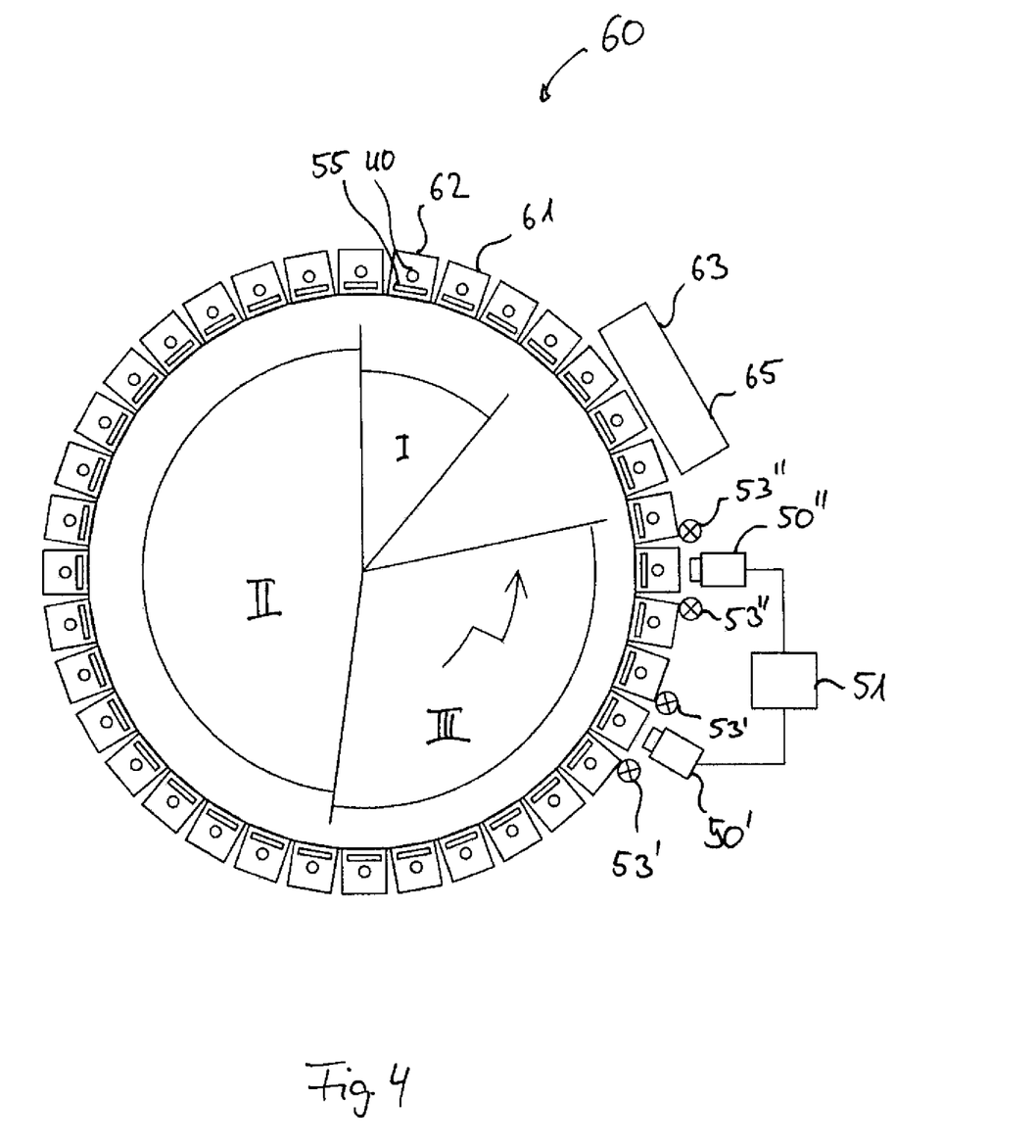
FIG. 4: a circular conveyor.

The hollow-fibre dialyzers are inserted into the receivers 61, 62 in a loading station 63. The circular conveyor 60 moves on one position in each case at set intervals, with the result that the next receiver 61, 62 can be loaded with a hollow-fibre dialyzer in the loading station 63.

The receivers 61, 62 are moved incrementally along the circular conveyor 60 and, among other things, pass through a preparation section I, and a sterilization section II, in which hot steam is channelled through the hollow-fibre dialyzer and the line system of the receivers 61, 62 in order to sterilize them. The steam advances into the sight glass 40, with the result that this is also completely filled with steam and sterilized.

In a checking section III, the section of the hollow-fibre dialyzer forming the flow path of the blood is flushed with sterile-filtered water. The steam collapses in the sight glass 40, with the result that it completely fills with water. In parallel, the section of the hollow-fibre dialyzer forming the flow path of the dialysis fluid is flushed with sterile-filtered air in order to expel the steam. Optionally, flushing with sterile-filtered water can also be effected here before the flushing with sterile-filtered air.

While passing through the flushing section, the receivers 61, 62 reach a first measurement position, at which a first camera 50' and first light sources 53' are arranged. The first camera 50' captures one or more images of the sight glass 40 at the first measurement position and forwards them to an image evaluation unit 51. The location of the boundary surface 42 in the first measurement position is determined by the image evaluation unit 51 and is recorded together with an identifier of the individual receiver 61, 62.

Towards the end of the flushing section, the receivers 61, 62 reach a second measurement position, at which a second camera 50" and second light sources 53" are provided. The second camera 50" captures one or more images of the sight glass 40 at the second measurement position and likewise forwards them to the image evaluation unit 51. The location of the boundary surface 42 in the second measurement position is determined by the image evaluation unit 51.

From the change of the location of the boundary surface 42 between the first measurement position and the second measurement position, the image evaluation unit 51 or a downstream controller determines the quantity of air that has penetrated into the hollow fibres 15 of the hollow-fibre dialyzer 1 during the transport from the first measurement position to the second measurement position. If the pulse rate of the circular conveyor 60 is known and constant, this quantity of air can be used directly as a criterion for the tightness of the hollow-fibre dialyzer 1. If the pulse rate is not known, a first time stamp can be saved together with the measurement result at the first measurement position, and a second time stamp can be saved together with the measurement result at the second measurement position. The throughput time of the hollow-fibre dialyzer can then be determined from the difference between the two time stamps and can be taken into account in the assessment.

If the quantity of air that has penetrated or the leak rate is above a predefined threshold value, the corresponding hollow-fibre dialyzer must be evaluated as not tight and excluded from further use.

After passing through the flushing section, the water is pushed out of the hollow-fibre dialyzer and the latter is removed from the circular conveyor in an unloading station 65, with the result that a further hollow-fibre dialyzer can be inserted into the corresponding receiver 61, 62. The loading station 63 and the unloading station 65 can be combined to form one station, as represented in FIG. 4.

The representation of the carousel 60 in FIG. 4 is again greatly simplified. The carousel 60 can have a substantially higher number of receivers 61, 62 in order to provide a sufficient throughput of hollow-fibre dialyzers 1. Between the checking section III and the unloading station 65, a drying section can be provided, which is not represented here. The relative lengths of the individual sections are not necessarily depicted to scale in FIG. 4. Lines and valves required for the functions known per se of the carousel are not represented for better clarity.

The invention claimed is:

1. A method for checking the integrity of a hollow-fibre fluid filter which is constructed from a plurality of hollow fibres enclosed by a membrane, with the steps of:
    perfusing the inside of the hollow fibres with a fluid and supplying the outside of the hollow fibres with a gas, or
    perfusing the outside of the hollow fibres with the fluid and
    supplying the inside of the hollow fibres with the gas, wherein in each case the gas has a higher pressure than the fluid, and
    determining a quantity of the gas which penetrates into the fluid through holes in the membrane,
    wherein,
    after flowing through the hollow-fibre fluid filter, the fluid is channelled through a bubble trap, and in that
    a gas volume collecting in the bubble trap during a predefined or predefinable reference period is determined.

2. The method according to claim 1, wherein
    an initial value of the gas volume is determined at the start of the reference period,
    a final value of the gas volume is determined at the end of the reference period, and
    in that the quantity of the gas that has penetrated into the fluid in the reference period is determined from the difference between the initial value and the final value.

3. The method according to claim 2, wherein a flow system comprising the bubble trap and the hollow-fibre fluid filter is arranged on a conveyor operated in a pulsed manner, which is moved on at least one conveying position during the reference period.

4. The method according to claim 1, wherein water is used as the fluid.

5. The method according to claim 1, wherein a line system comprising the bubble trap and the hollow-fibre fluid filter is supplied with steam before the start of the check.

6. The method according to claim 1, wherein the determination of the volume of the gas collected in the bubble trap is effected visually.

7. The method according to claim 6, wherein the bubble trap has a transparent section, and in that, for the determination of the volume of the gas collected in the bubble trap, the location of a fluid surface in the transparent section is assessed.

8. The method according to claim 7, wherein
    at least one first camera image of the transparent section is captured at the start of the reference period and the initial location of the fluid surface is determined by means of an image evaluation method,
    at least one second camera image of the transparent section is captured at the end of the reference period and the final location of the fluid surface is determined by means of the image evaluation method, and in that
    the volume of the gas collected is determined from the initial location of the fluid surface and the final location of the fluid surface.

9. The method according to claim 8, wherein the first and the second camera image are captured using a transmitted light method.

10. The method according to claim 9, wherein the illumination is effected by means of a fluorescent film, which is illuminated with excitation light of a first wavelength, and which, in response to the illumination with excitation light, emits fluorescent light of a second wavelength, wherein the second wavelength is greater than the first wavelength, and wherein the camera images are captured through a color filter that is not transparent for light of the first wavelength.

11. An equipment for checking the integrity of a hollow-fibre fluid filter, which is constructed from a plurality of hollow fibres enclosed by a membrane, comprising:
    a flushing system which is set up to channel a fluid through the interior of the hollow fibres of the hollow-fibre fluid filter to be checked and
    a gas pressure system which is set up to supply the exterior of the hollow fibres of the hollow-fibre fluid filter to be checked with a gas, or
    the flushing system which is set up to channel the fluid through the exterior of the hollow fibres of the hollow-fibre fluid filter to be checked and
    the gas pressure system which is set up to supply the interior of the hollow fibres of the hollow-fibre fluid filter to be checked with the gas,
    wherein in each case the pressure of the gas is higher than the pressure of the fluid, and
    a measuring device for the determination of a quantity of the gas penetrating into the fluid through holes in the membrane during a predefined or predefinable reference period,
    wherein
    the flushing system comprises a bubble trap arranged downstream of the hollow-fibre fluid filter, and
    in that the measuring device is set up to determine a volume of the gas collecting in the bubble trap during the predefined or predefinable reference period.

12. The equipment according to claim 11, wherein the measuring device is set up
    to determine an initial value of the gas volume at the start of the reference period,
    to determine a final value of the gas volume at the end of the reference period, and
    to determine the quantity of the gas that has penetrated into the hollow fibres in the reference period from the difference between the initial value and the final value.

13. The equipment according to claim 11, wherein the measuring device is set up to determine the volume of the gas collecting in the bubble trap visually.

14. The equipment according to claim 13, wherein the bubble trap has a transparent section, and in that, for the determination of the volume of the gas collected in the bubble trap, the measuring device is set up to assess the location of a fluid surface in the transparent section.

15. The equipment according to claim 14, wherein the measuring device comprises at least one camera and an image evaluation system.

16. The equipment according to claim 15, wherein the measuring device comprises at least one fluorescent film and at least one source for excitation light.

17. The equipment according to claim 15, wherein the measuring device comprises a first camera which is arranged stationary adjacent to a conveying path of the conveying system.

18. The equipment according to claim 17, wherein the measuring device comprises a second camera which is arranged stationary adjacent to the conveying path of the conveying system.

19. The equipment according to claim 17, wherein the first and/or the second camera are arranged adjacent to a stopping position of the conveying system.

20. The equipment according to claim 11, further comprising a plurality of the hollow-fibre fluid filter and a plurality of the bubble trap and wherein the equipment is a component of a conveying system driven in a pulsed manner, and comprises several conveying elements, wherein each conveying element is provided for receiving at least one of the plurality of the hollow-fibre fluid filter, and wherein each conveying element comprises, for each hollow-fibre fluid filter to be received, one of the plurality of the bubble trap which is movable along the conveying system together with the hollow-fibre fluid filter.

21. The equipment according to claim 20, wherein the conveying system is a circular conveyor.

* * * * *